United States Patent [19]

Okada et al.

[11] Patent Number: 4,768,505
[45] Date of Patent: Sep. 6, 1988

[54] CALCULUS CRUSHING APPARATUS

[75] Inventors: Tsutomu Okada; Mikio Utsugi, both of Tokyo, Japan

[73] Assignee: Olympus Optical Co., Ltd., Tokyo, Japan

[21] Appl. No.: 42,476

[22] Filed: Apr. 24, 1987

[30] Foreign Application Priority Data

May 2, 1986 [JP] Japan .................................. 61-102462
May 8, 1986 [JP] Japan .................................. 61-105291

[51] Int. Cl.<sup>4</sup> .............................................. A61B 17/22
[52] U.S. Cl. ...................................... 128/328; 128/320
[58] Field of Search ................................. 128/328, 320

[56] References Cited

U.S. PATENT DOCUMENTS 1,612,697 12/1926 Cecil .................................... 128/328
1,677,671 7/1928 Councill ............................... 128/328

FOREIGN PATENT DOCUMENTS

32068 4/1983 Fed. Rep. of Germany .
860406 5/1986 Fed. Rep. of Germany .
2449988 5/1983 Japan .

Primary Examiner—Michael H. Thaler
Attorney, Agent, or Firm—Ladas & Parry

[57] ABSTRACT

A calculus crushing apparatus includes a flexible sheath for insertion into a body cavity and an operation wire slidably inserted in the sheath. A basket for holding a calculus is fixed to the distal end of the operation wire. The basket is formed of a plurality of elastic wires. A connecting rod is connected to the proximal end of the operation wire. By moving the connecting rod by an operation mechanism, the operation wire slides in the sheath, so that the basket is projected from or retracted in the sheath. The connecting rod has a disconnecting portion which is weaker than the elastic wires and operation wire against tension.

13 Claims, 9 Drawing Sheets

CALCULUS CRUSHING APPARATUS

BACKGROUND OF THE INVENTION

The present invention relates to a calculus crushing apparatus for crushing a calculus produced in a body cavity. A calculus produced in internal organs such as a bile duct or a urinary bladder adversely affects a patient. Especially, an enlarged calculus gives much pain to a patient. Therefore, a calculus crushing apparatus is inserted in a body cavity through an endoscope and crushes the calculus produced in the body cavity to remove it from the body or removes it without crushing.

A calculus crushing apparatus of this type includes a sheath having a hard portion at its distal end and inserted in a body cavity with an endoscope, an operation wire inserted in the sheath, and a basket constituted by a plurality of elastic wires and fixed at the distal end of the operation wire. A connecting rod is fixed to the proximal end of the operation wire and is reciprocated by an operation section to expand or contract the basket. In crushing a calculus, after the calculus is held inside the basket projected from the distal end of the sheath, the basket is retracted inside the sheath and contracted by the operation portion, so that the calculus is crushed into pieces by the basket.

If a calculus held inside the basket is very hard, a very large tension acts on the basket, operation wire, and connecting rod when the basket is retracted inside the sheath. For this reason, the elastic wires of the basket or the operation wire may be disconnected midway therealong by the tension. When the elastic wires are disconnected, the wall of the body cavity is damaged by disconnected portions. On the other hand, when the operation wire is disconnected midway therealong with the calculus held inside the basket, the basket and the part of the operation wire cannot be pulled outside the body cavity and remain therein, thereby posing a serious problem.

SUMMARY OF THE INVENTION

The present invention has been made in consideration of the above circumstances, and has as its object to provide a calculus crushing apparatus which can prevent disconnection of the basket and the operation wire even when a large tension acts thereon during a crushing operation.

In order to achieve the above object, a calculus crushing apparatus of the present invention comprises a basket connected to the distal end of an operation wire and constituted by a plurality of elastic wires, and an elongated connecting member connected to the proximal end of the operation wire. The connecting member has a disconnecting portion with a strength lower than those of the elastic wires and the operation wire against tension.

When a large tension acts on the elastic wires, operation wire, and connecting member during crushing a hard calculus, the connecting member is disconnected at the disconnecting portion before the elastic wires or the operation wire is disconnected. As a result, disconnection of the elastic wires or the operation wire can be prevented.

BRIEF DESCRIPTION OF THE DRAWINGS

FIGS. 1 to 9 show a calculus crushing apparatus according to an embodiment of the present invention, in which

FIGS. 20 and 21 show a modification of the basket, in which

DETAILED DESCRIPTION OF THE PREFERRED EMBODIMENT

An embodiment of the present invention will now be described in detail with reference to the accompanying drawings.

Figure 1:
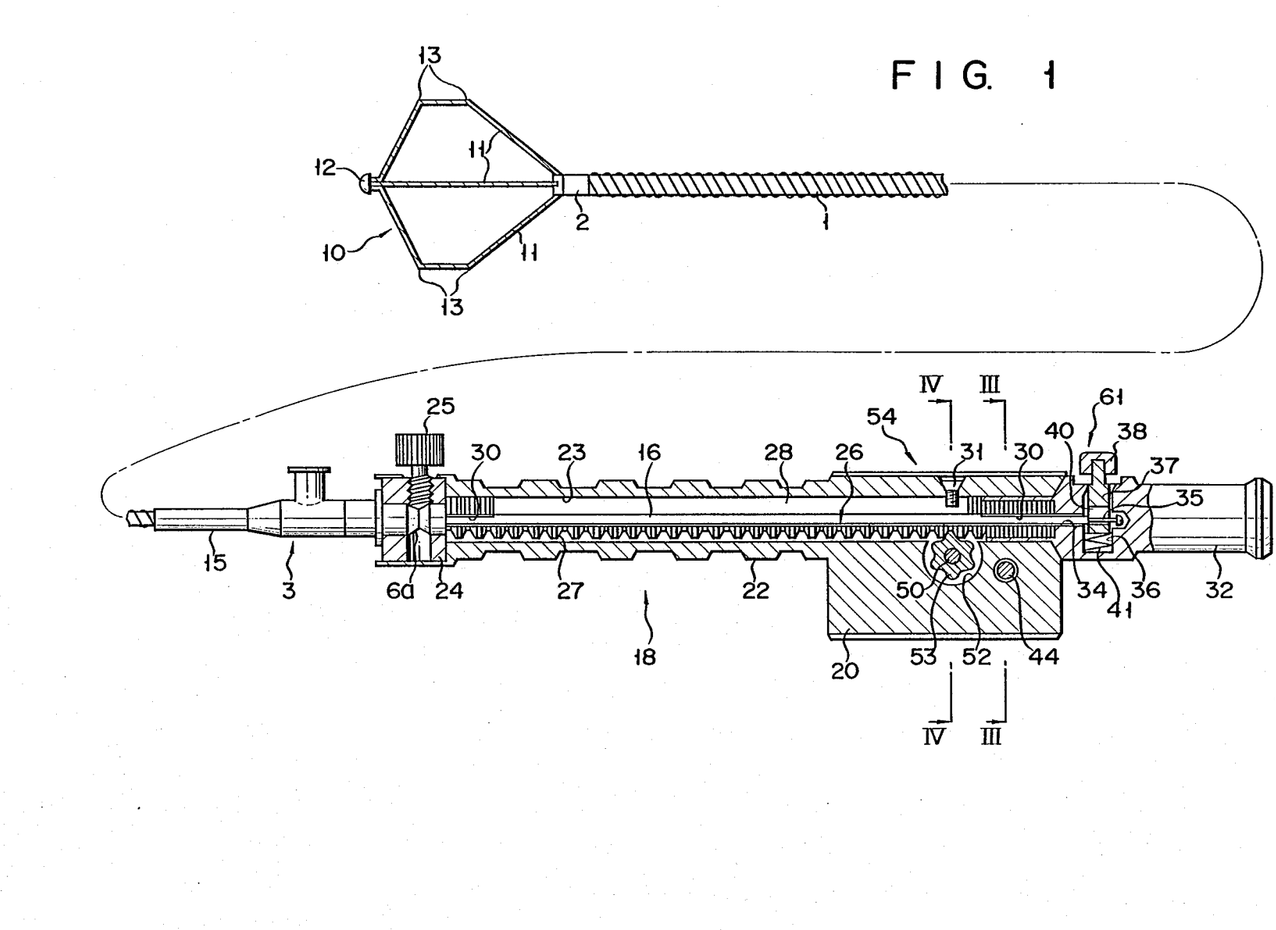
FIG. 1 is a partially cutaway side view of the entire apparatus.
Figure 2:
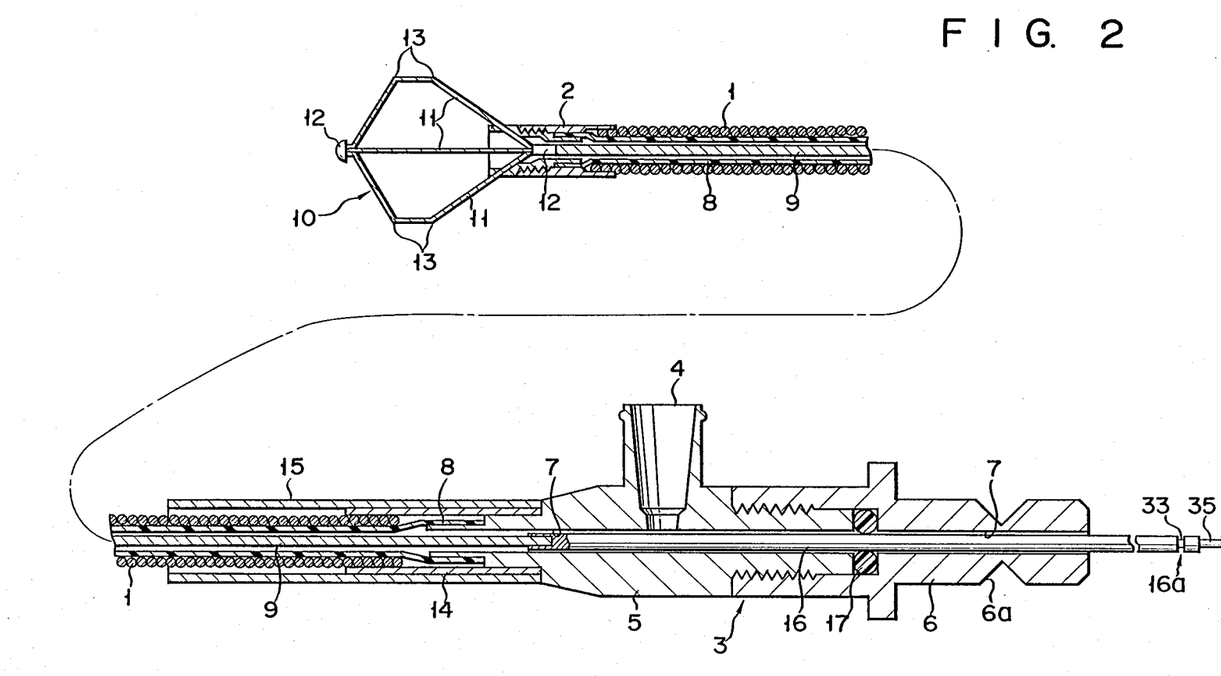
FIG. 2 is a sectional view of a sheath of the apparatus.

As is shown in FIGS. 1 and 2, a calculus crushing apparatus includes flexible sheath 1 formed of, e.g., a closely wound coil. Tubular hard portion 2 made of stainless steel or the like is fixed to the distal end of sheath 1, and mouthpiece 3 is fixed to its proximal end. As is shown in FIG. 2, mouthpiece 3 includes first member 5 having liquid supply portion 4 and connected to the proximal end of sheath 1, and second member 6 threadably engaged with member 5. Through hole 7 is coaxially formed through members 5 and 6. Liquid-tight tube 8 inserted inside sheath 1 is connected to member 5 and communicates with hole 7. Tube 8 extends from mouthpiece 3 to the distal end of sheath 1. Therefore, a syringe (not shown) may be connected to member 4 of mouthpiece 3 to supply a liquid such as a contrast medium to tube 8. The proximal end of sheath 1 is inserted and fixed in mounting pipe 14 extending from member 5. In addition, the proximal end of sheath 1 is protected by cover 15 provided outside pipe 14.

Operation wire 9 longer than sheath 1 is slidably inserted therein. Basket 10 for holding and crushing a calculus is fixed to the distal end of wire 9, i.e., the end located at the side of hard portion 2. More specifically, basket 10 is constructed by connecting both ends of a plurality of elastic wires 11 with tips 12 and forming bent portions 13 midway along respective wires 11, and can be expanded/contracted, i.e., opened/closed.

The distal end of elongated straight connecting rod 16 is fixed to the proximal end of wire 9 projecting from the rear end of sheath 1. Rod 16 is slidably inserted in hole 7 of mouthpiece 3, and projects from member 6. O-ring 17 is provided at the connecting portion between members 5 and 6 of mouthpiece 3 so that hole 7 is maintained liquid-tight. Rod 16 extends through O-ring 17.

Mouthpiece 3 is detachably connected to operation portion 18. As is shown well in FIG. 1, portion 18 includes main body 20 and grip portion 22 extending from body 20 to be held by an operator. Insertion hole 23 is formed through body 20 and portion 22 along an extending direction of portion 22. Connecting ring 24 is mounted on the distal end of portion 22 coaxially with hole 23. Set screw 25 is screwed in ring 24 to be radially reciprocated. The rear end of member 6 of mouthpiece 3 is inserted in ring 24, and screw 25 is screwed therein so that its distal end engages with groove 6a formed in the outer surface of the rear end of member 6, thereby connecting mouthpiece 3 with portion 18. When mouthpiece 3 is connected to portion 18, rod 16 is inserted in hole 23.

Figure 3:
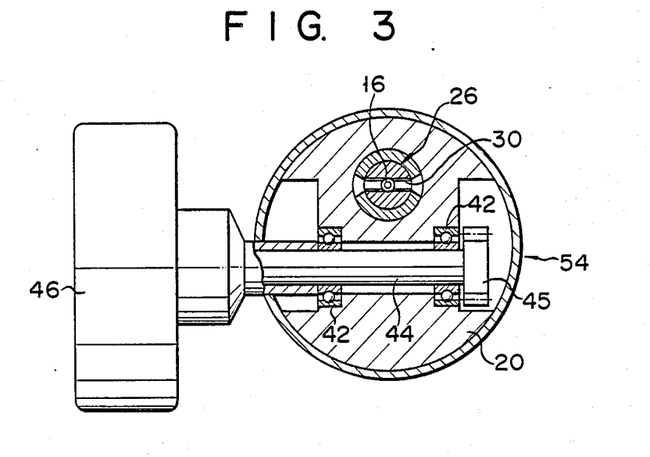
FIG. 3 is a sectional view taken along line III—III of FIG. 1.
Figure 4:
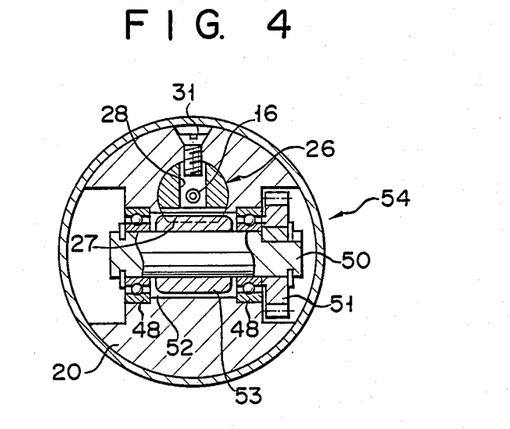
FIG. 4 is a sectional view taken along line IV—IV of FIG. 1.

As is shown in FIGS. 1, 3, and 4, rack 26 is slidably inserted in hole 23 of portion 18. Rack 26 has a substantially circular cross-section, and teeth 27 are formed on one radial side substantially throughout the entire axial length of rack 26. Guide groove 28 opened at an outer surface opposite to the side of teeth 27 is axially formed in rack 26 except its axial both ends. Through holes 30 are formed in the axial both ends of rack 26 coaxially with hole 23 and respectively communicate with groove 28. Guide screw 31 screwed in body 20 of portion 18 engages with groove 28 of rack 26, thereby preventing rotation of rack 26 in hole 23 and rack 26 from coming out hole 23. The rear end portion of rod 16 extending from mouthpiece 3 is inserted in hole 30 and groove 28 and its extreme end projects from the rear end of rack 26.

Holding portion 32 for sliding rack 26 is connected to the rear end of rack 26 and projects from body 20 of portion 18. Mounting hole 34 is formed in portion 32 coaxially with hole 30 of rack 26 and communicates with groove 28 through hole 30. The end of rod 16 having flat portion 35 (see FIG. 2) is inserted in hole 34. Housing hole 36 is formed radially along portion 32 to across hole 34 and is opened at an outer surface of portion 32. Locking rod 37 having button 38 at its upper end is inserted in hole 36. Rod 37 has engaging hole 40 formed through an axial midway portion thereof and is biased in a direction to project from portion 32 by spring 41 provided in hole 36. In order to connect rod 16 to portion 32, first, rod 37 is pressed against spring 41 so that holes 40 and 34 are aligned with each other. Then, the rear end of rod 16 is inserted in hole 34 to place portion 35 at a position of hole 40, and the force applied to rod 37 is released, thereby engaging portion 35 of rod 16 with rod 37 to connect rod 16 with portion 32. Therefore, wire 9 can be reciprocated through rod 16 by operating portion 32. As is shown in FIG. 2, notch 33 is formed in the outer surface of the proximal end of rod 16 to constitute disconnecting portion 16a according to the present invention. Against tension, portion 16a is weaker than the elastic wires constituting basket 10 and wire 9, and is the weakest portion of rod 16.

In body 20 of portion 18, as is shown in FIG. 3, first support shaft 44 is rotatably supported by bearings 42 and extends in a direction perpendicular to rack 26. First gear 45 is fixed to one end of shaft 44, and handle 46 disposed outside body 20 is mounted on the other end thereof. As is shown in FIG. 4, second support shaft 50 is rotatably supported by bearings 48 in body 20 and extends parallel to shaft 44. Gear 51 engaging with gear 45 and having teeth more than those of gear 45 is mounted on one end of shaft 50. Cavity 52 is formed in body 20. It is located at the side of teeth 27 of rack 26 and opens in hole 23. Shaft 50 extends through cavity 52. Third gear 53 fitted on shaft 50 is housed in cavity 52 and meshes with teeth 27 of rack 26. Therefore, when handle 46 is rotated, this rotation is decelerated by gears 45 and 50 and transmitted to gear 53. Thus, rack 26 is moved by gear 53, thereby moving wire 9 forward or backward through rod 16. Gears 45, 51, and 53 constitute reduction gear mechanism 54.

Figure 5:
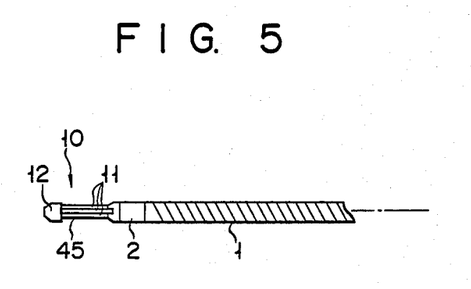
FIG. 5 is a side view of the distal end of the sheath with a basket closed.

The movement of rack 26 is guided by screw 31 engaging with groove 28. That is, as is shown in FIG. 1, when rack 26 moves forward to expand basket 10, the rear end of groove 28 approaches screw 31. When rack 26 is to be moved forward further, holding portion 32 abuts against the rear end of body 20, thereby preventing further movement of rack 26. On the contrary, when rack 26 is moved backward to close basket 10, tip 12 of basket 10 abuts against hard portion 2 of sheath 1, thereby preventing further movement of rack 26. When rack 26 is moved backward, basket 10 is retracted inside sheath 1 through wire 9 and is closed as is shown in FIG. 5. The distal end portion of basket 10 projects from portion 2 at the distal end of sheath 1. The projecting portion of basket 10 constitutes guide portion 45 serving as a guide when sheath 1 is inserted in a body cavity. Since basket 10 is constituted by elastic wires 11, portion 45 is softer than sheath 1 formed of a closely wound coil.

An operation of the calculus crushing apparatus having the above arrangement will be described.

First, sheath 1 is inserted in an insertion channel (not shown) of an endoscope with basket 10 closed as is shown in FIG. 5 and is then inserted in a body cavity together with the endoscope. Thereafter, as is shown in FIG. 6, the distal end portion of sheath 1 is projected from the distal end of endoscope 56 and is inserted in bile duct 60 through duodenal papilla 58.

When sheath 1 is to be inserted in the body cavity, guide portion 45 projecting from the distal end of sheath 1 guides insertion of sheath 1. That is, if the insertion channel of endoscope 56 is bent when sheath 1 is to be inserted therein, portion 45 abuts against the inner wall of the bent portion of the channel and is deformed therealong. Therefore, by further pushing sheath 1 in this state, sheath 1 is guided by portion 45 to move forward in the insertion channel. Thus, even if the insertion channel is bent, sheath 1 can be inserted in the channel without damaging the inner wall of the channel.

Figure 6:
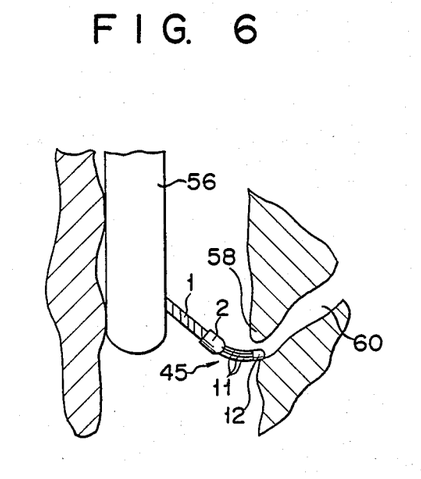
FIG. 6 is a schematic view for explaining how the distal end of the sheath is inserted inside a bile duct.

In addition, as is shown in FIG. 6, when sheath 1 is to be inserted in a narrow portion such as bile duct 60, guide portion 45 deforms at an entrance of bile duct 60 along its extending direction to guide insertion of sheath 1. Therefore, the distal end of sheath 1 can be easily inserted in bile duct 60 without damaging the inner wall of the body cavity.

Figure 7:
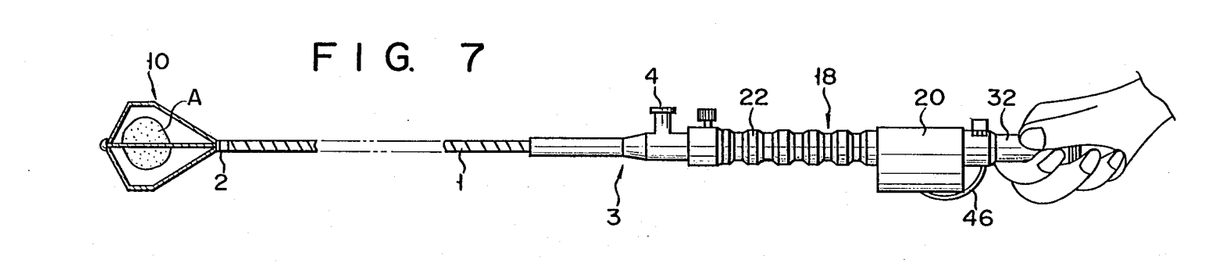
FIGS. 7 to 9 are sectional views of the apparatus in different operation states.
Figure 8:
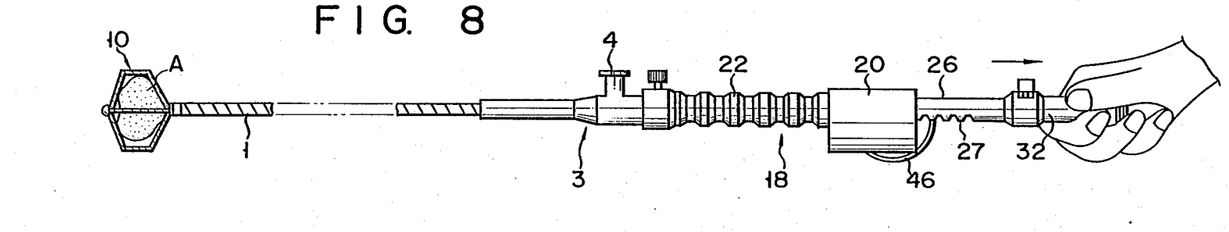

Then, an interior of bile duct 60 is observed by endoscope 56. If calculus A is found, holding portion 32 is pushed into body 20 to move wire 9 forward together with rack 26, as is shown in FIG. 7. Then, basket 10 is projected from the distal end of sheath 1 and is opened. After basket 10 is opened, calculus A is taken in basket 10 through a gap between wires 11, and portion 32 is pulled out from body 20 to contract basket 10, as is shown in FIG. 8. A reciprocation operation of wire 9 so far can be quickly and easily performed by holding portion 32. Therefore, if basket 10 fails to take in calculus A, this taking-in operation can be easily performed again.

Figure 9:
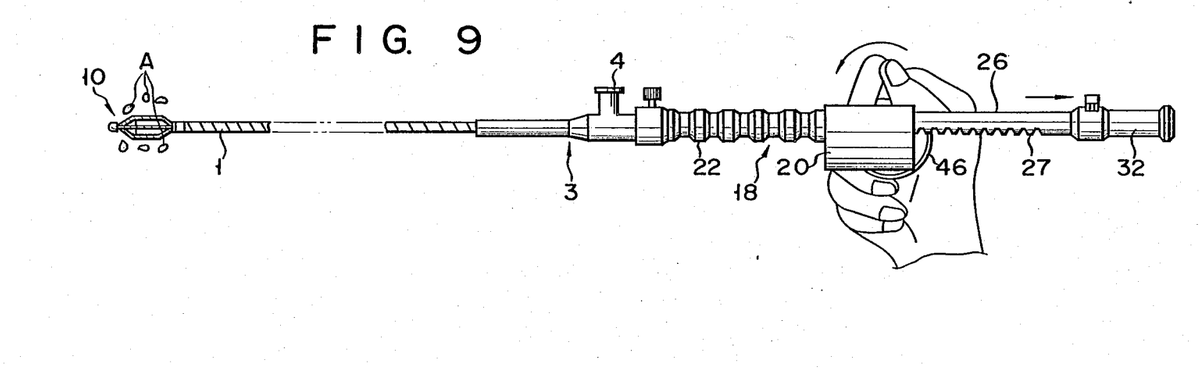

If calculus A held inside basket 10 in this manner is too large to be removed through bile duct 60, handle 46 of operation section 18 is rotated in a direction in which rack 26 moves backward, i.e., rack 26 projects from body 20, as is shown in FIG. 9. Then, upon movement of rack 26, rod 16 and wire 9 retract basket 10 inside sheath 1, so that basket 10 is contracted. Therefore, calculus A is clamped and crushed by wires 11 of basket 10. At this time, the rotation speed of handle 46 is reduced by mechanism 54 and then transmitted to rack 26. For this reason, the moving speed of rack 26, i.e., contracting speed of basket 10 is slower than the rotation speed of handle 46. Therefore, calculus A is crushed at low speed, so that it is not spread forcibly upon breaking and does not damage the inner wall of bile duct 60. In addition, operation force applied to handle 46 is amplified by mechanism 54, i.e., gears 45, 51, and 53 and then transmitted to rack 26. Therefore, if handle 46 is rotated by a relatively small force, calculus A can be sufficiently crushed.

Calculus A may be crushed by another method in which calculus A is held inside basket 10 and holding portion 32 is slid back and forth to cause calculus A to repeatedly strike against hard portion 2 provided at the distal end of sheath 1.

During the crushing operation of calculus A, if calculus A is very hard, handle 46 must be rotated by a force larger than usual. Therefore, a large tension acts on basket 10, wire 9, and rod 16. When a tension significantly larger than that required for crushing a calculus with normal hardness acts on these members, rod 16 is disconnected at portion 16a before wires 11 or wire 9 is disconnected. When rod 16 is disconnected, operation section 18 is detached from mouthpiece 3. As a result, a portion of rod 16 connected to wire 9 is exposed outside from mouthpiece 3. In this state, rod 16 is held by a hand to move wire 9 back and forth, and calculus A is removed from basket 10. Therefore, basket 10 can be retracted inside sheath 1, and basket 10, wire 9, and sheath 1 can be pulled out from the body cavity.

According to the calculus crushing apparatus having the above arrangement, the connecting rod has a disconnecting portion weaker against tension than the elastic wires constituting the basket and the operation wire. Therefore, if a very large tension acts on the basket, the operation wire, and the connecting rod during the calculus breaking operation, the connecting rod is disconnected at the disconnecting portion before the elastic wires or the operation wire is disconnected. As a result, the inner wall of the body cavity will not be damaged, and the operation wire and the basket will not remain inside the body cavity because the elastic wires or the operation wire is not disconnected.

In addition, since the crushing apparatus has the guide portion projecting from the distal end of the sheath, the sheath can be easily inserted in a bent or narrow portion.

Note that the present invention is not limited to the above embodiment, but can be variously modified without departing from the spirit and scope of the present invention.

Figure 10:
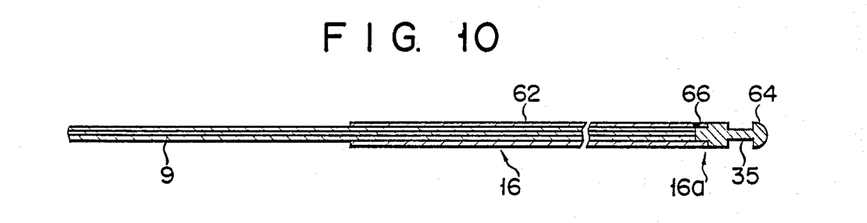
FIGS. 10 and 11 are sectional views respectively showing first and second modifications of a disconnecting portion.

According to a first modification shown in FIG. 10, connecting rod 16 includes cylindrical main body 62 and fixing member 64 having flat portion 35 and connected to the proximal end of body 62, and the proximal end of operation wire 9 is inserted and fixed in body 62. Member 64 is connected to body 62 by, e.g., brazing, and connecting portion 66 constitutes disconnecting portion 16a.

Figure 11:
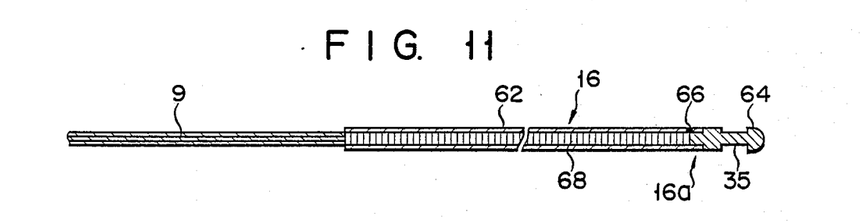

Note that in the first modification, a brazing material may be coated on that portion of wire 9 which is inserted in body 62 of rod 16, as shown is in FIG. 11, and entire coating portion 68 may be brazed to body 62.

Figure 12:
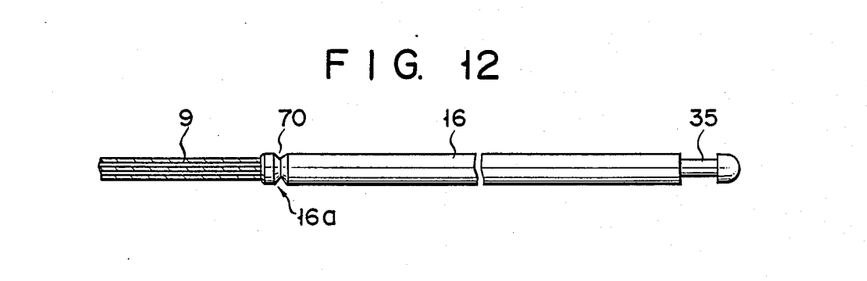
FIGS. 12 and 13 are sectional views respectively showing third and fourth modifications of the disconnecting portion.

According to a third modification shown in FIG. 12, disconnecting portion 16a is formed at the distal end of rod 16, i.e., the end at the side of wire 9. Portion 16a is constituted by V-shaped groove 70 extending throughout the outer periphery of rod 16.

In the third modification, rod 16 is disconnected at portion 16a, i.e., at its distal end when a large tension acts thereon during the crushing operation. When rod 16 is disconnected and the disconnected portion is not exposed after the operation section is detached from the mouthpiece, the sheath is further pulled out from the operation wire. In this case, since a hard connecting rod, which is intended to prevent the pulling-out operation, is not present, the sheath can be easily pulled out. By pulling out the sheath, the disconnected portion, i.e., the proximal end of the operation wire is exposed outside, and the calculus can be removed from the basket by operating the operation wire.

Figure 13:
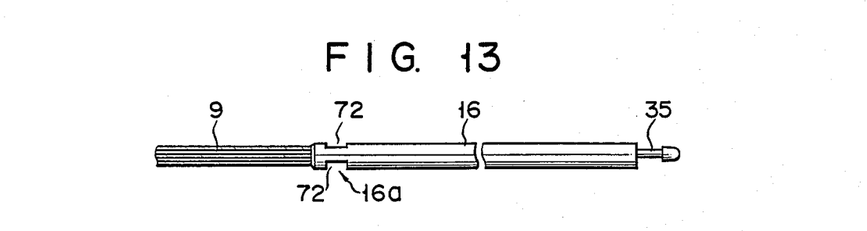

As is shown in FIG. 13, disconnecting portion 16a may be formed by notch 72.

Figure 14:
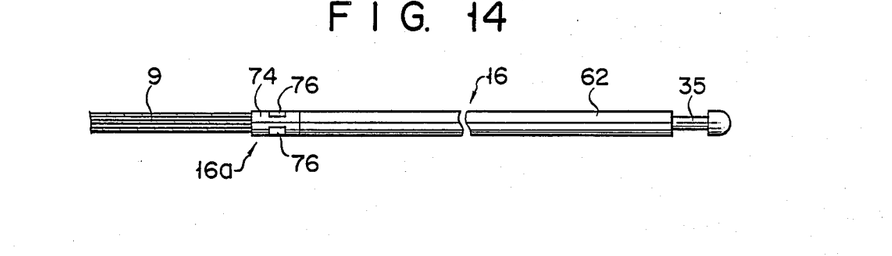
FIGS. 14 and 15 are side and exploded perspective views, respectively, showing a fifth modification of the disconnecting portion.
Figure 15:
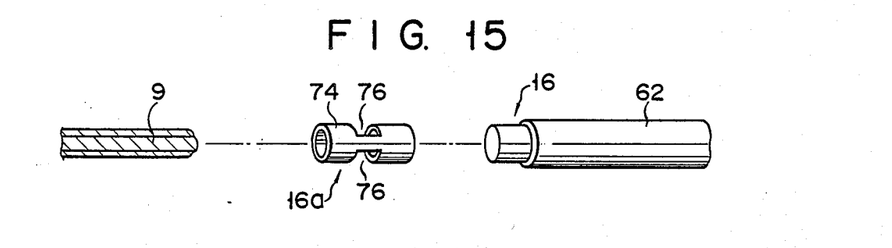

According to a fifth modification shown in FIGS. 14 and 15, rod 16 includes cylindrical main body 62 and connecting pipe 74 connected to body 62, and the proximal end of operation wire 9 is connected to pipe 74. A plurality of notches 76 are formed in pipe 74 to constitute disconnecting portion 16a.

Figure 16:
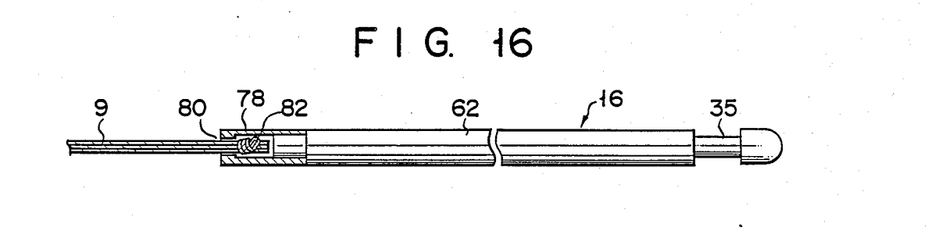
FIGS. 16 and 17 are partially cutaway side and exploded perspective views, respectively, showing a sixth modification of the disconnecting portion.
Figure 17:
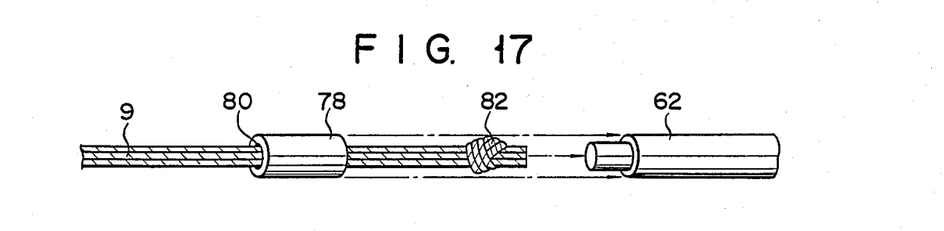

According to a sixth modification shown in FIGS. 16 and 17, connecting rod 16 includes main body 62 and cap 78 fixed to the distal end of body 62, and through hole 80 is formed in cap 78. The proximal end of operation wire 9 is tied to form knot 82, and cap 78 covers knot 82 with wire 9 inserted in hole 80. Note that hole 80 is formed to have a diameter such that knot 82 cannot pass therethrough.

According to the sixth modification, when a very large tension acts on wire 9 and rod 16, knot 82 is untied and passes through cap 80, thereby disconnecting wire 9 and rod 16.

Figure 18:
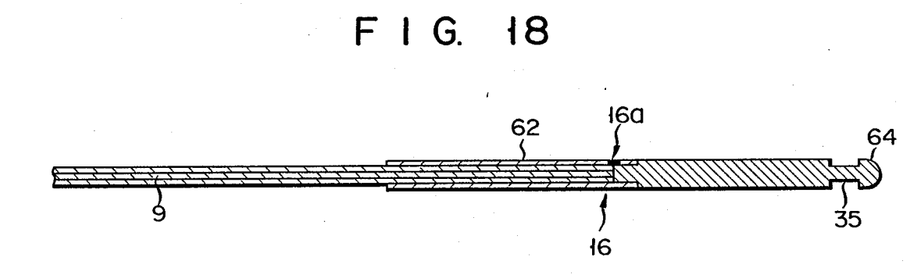
FIGS. 18 and 19 are sectional views respectively showing seventh and eighth modifications of the disconnecting portion.
Figure 19:
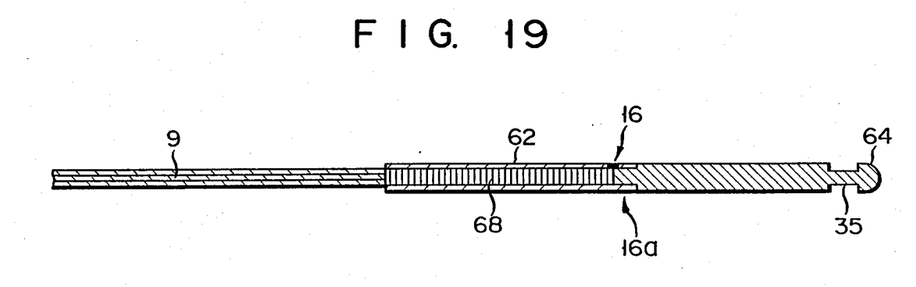

Further, disconnecting portion 16a may be provided at a midway along connecting rod 16, as is shown in FIGS. 18 and 19.

Figure 20:
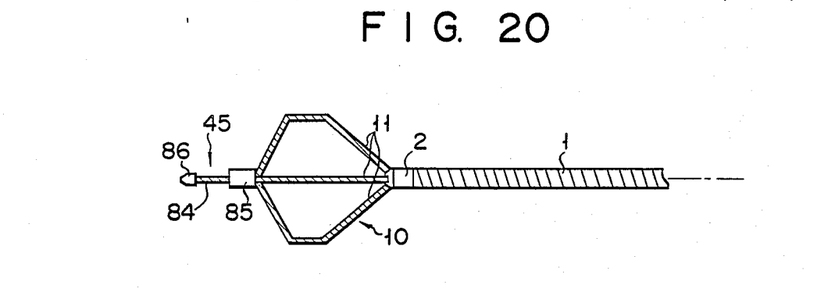
FIG. 20 is a side view showing the opened basket.
Figure 21:
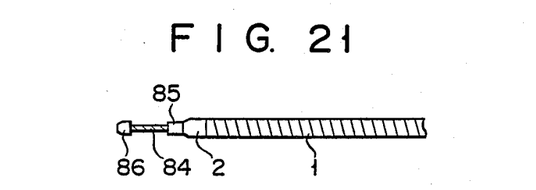
FIG. 21 is a side view showing the closed basket.

In the above embodiment, guide portion 45 is formed by the distal end of basket 10. However, as is shown in FIGS. 20 and 21, portion 45 may be formed by wire 84 separate from basket 10. That is, the distal ends of elastic wires 11 constituting basket 10 are connected by ring 85 with each other, and wire 84 extends from ring 85. Tip 86 is mounted on the distal end of wire 84. Wire 84 is formed softer than sheath 1.

When basket 10 is retracted inside sheath 1 and is closed, ring 85 abuts against hard portion 2 at the distal end of sheath 1, thereby preventing further retraction of the operation wire. In this state, only wire 84 projects from the distal end of sheath 1.

Figure 22:
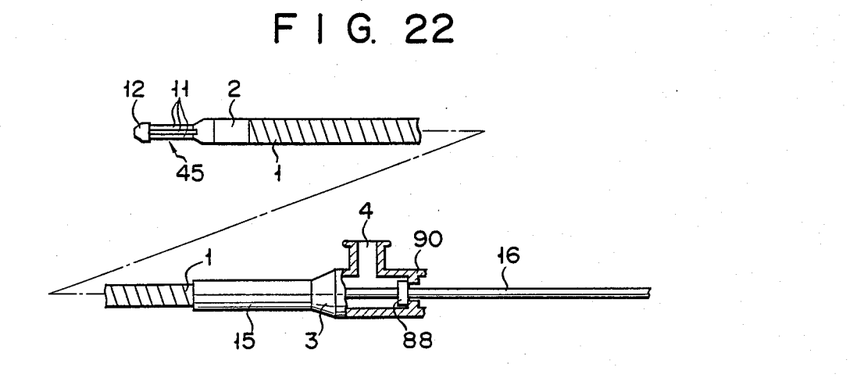
FIG. 22 is a partially cutaway view showing a modification of the sheath.

According to a modification shown in FIG. 22, first stopper 88 fixed at the distal end of connecting rod 16 and second stopper 90 formed on an inner surface of mouthpiece 3 are arranged so as to control movement of the rack, or the operation wire. When stopper 88 abuts against stopper 90, basket 10 is closed, and only the distal end of basket 10 forming guide portion 45 projects from the distal end of sheath 1. For this reason, even when operation section 18 having guide groove 23 and guide screw 31 which constitute the controlling means is detached from mouthpiece 3, movement of wire 9 and basket 10 can be reliably controlled.

What is claimed is:

1. A calculus crushing apparatus for crushing a calculus produced in a body cavity, comprising:
    a flexible sheath having a hard portion at its distal end and to be inserted in the body cavity;
    an operation wire slidably inserted in the sheath;
    a basket for holding the calculus and capable of expansion and contraction, the basket being constituted by a plurality of elastic wires and connected to the distal end of the operation wire;
    an elongated connecting member connected to the proximal end of the operation wire and extending outward from the proximal end of the sheath, the connecting member having a disconnecting portion with a strength lower than those of the elastic wires and the operation wire against tension; and
    operating means for sliding the operation wire with respect to the sheath through the connecting member so as to make the basket project from or retract in the sheath.

2. An apparatus according to claim 1, wherein said connecting member includes a distal end located at the side of the operation wire and a proximal end, and the disconnecting portion is formed near the proximal end of the connecting member.

3. An apparatus according to claim 1, wherein said connecting member includes a distal end located at the side of the operation wire and a proximal end, and the disconnecting portion is formed near the distal end of the connecting member.

4. An apparatus according to claim 1, wherein said disconnecting portion is formed at a midway portion along the connecting member.

5. An apparatus according to claim 1, wherein said disconnecting portion is formed by forming a groove in an outer surface of the connecting member.

6. An apparatus according to claim 1, wherein said disconnecting portion is formed by forming a notch in an outer surface of the connecting member.

7. An apparatus according to claim 1, wherein said connecting member includes a cylindrical main body and a fixing member connected to one end of the main body, the proximal end of the operation wire is inserted in the main body from the other end of the main body and fixed therein, and a connecting portion between the main body and the fixing member constitutes the disconnecting portion.

8. An apparatus according to claim 1, wherein said connecting member includes a main body and a connecting pipe having one end connected to one end of the main body and the other end connected to the proximal end of the said operation wire, and the disconnecting portion formed in the connecting pipe.

9. An apparatus according to claim 1, wherein said connecting member includes a main body and a cap connected to one end of the main body, the proximal end of the operation wire is tied to form a knot, and the cap includes a through hole having such diameter that the knot cannot pass therethrough, and covers the knot with the operation wire passed through the through hole.

10. An apparatus according to claim 1, which further comprises: a guide portion for guiding insertion of the sheath to a desired portion, the guide portion being provided to project from the distal end of the sheath when the basket is closed.

11. An apparatus according to claim 10, which further comprises: means for positioning the basket such that the basket is closed and the distal end portion of the basket projects from the distal end of the sheath, the guide portion being constituted by the distal end portion of the basket.

12. An apparatus according to claim 10, wherein said basket includes a stopper which abuts against the distal end of the sheath when the basket is retracted inside the sheath, and the guide portion includes a flexible wire projecting from the stopper.

13. An apparatus according to claim 1, wherein said operating means includes a main body detachably connected to the proximal end of the sheath, a rack slidably provided in the main body, a plurality of gears provided in the main body and meshing with the rack, and a handle provided at the main body to be operated from outside the main body and connected to the gears, for rotating the gears; and the connecting member is inserted in the main body, extends parallel to the rack, and is detachably connected at its proximal end to the rack so as to move together therewith.

* * * * *